(12) United States Patent
Sterling et al.

(10) Patent No.: US 7,674,396 B2
(45) Date of Patent: *Mar. 9, 2010

(54) METHOD AND SYSTEM FOR TREATMENT OF EATING DISORDERS

(75) Inventors: Bernhard B. Sterling, Danville, CA (US); Alexander K. Mills, San Antonio, CA (US)

(73) Assignee: Plensat LLC, Danville, CA (US)

( * ) Notice: Subject to any disclaimer, the term of this patent is extended or adjusted under 35 U.S.C. 154(b) by 889 days.

This patent is subject to a terminal disclaimer.

(21) Appl. No.: 11/270,397

(22) Filed: Nov. 8, 2005

(65) Prior Publication Data

US 2007/0104754 A1    May 10, 2007

(51) Int. Cl.
*C09K 3/00* (2006.01)
*A61K 9/12* (2006.01)
*A61K 33/10* (2006.01)

(52) U.S. Cl. .................... 252/183.16; 424/44; 424/687; 424/717

(58) Field of Classification Search ........................ None
See application file for complete search history.

(56) References Cited

U.S. PATENT DOCUMENTS

| 5,055,306 | A | | 10/1991 | Barry et al. | |
|---|---|---|---|---|---|
| 5,084,061 | A | | 1/1992 | Gau et al. | |
| 5,750,585 | A | * | 5/1998 | Park et al. | 521/143 |
| 5,780,057 | A | | 7/1998 | Conte et al. | |
| 6,077,540 | A | * | 6/2000 | Daher et al. | 424/478 |
| 6,271,278 | B1 | * | 8/2001 | Park et al. | 521/150 |
| 6,326,028 | B1 | * | 12/2001 | Nivaggioli et al. | 424/481 |
| 6,432,448 | B1 | * | 8/2002 | Augello et al. | 424/479 |
| 6,503,264 | B1 | | 1/2003 | Birk | |
| 6,861,072 | B1 | * | 3/2005 | Alaux et al. | 424/472 |
| 2003/0070584 | A1 | * | 4/2003 | Gulian et al. | 106/162.8 |
| 2004/0219186 | A1 | | 11/2004 | Ayres | |
| 2007/0078476 | A1 | * | 4/2007 | Hull et al. | 606/191 |
| 2008/0107732 | A1 | * | 5/2008 | Dharmadhikari et al. | 424/482 |
| 2008/0208240 | A1 | * | 8/2008 | Paz | 606/191 |

FOREIGN PATENT DOCUMENTS

EP    103481 A1 *    3/1984

OTHER PUBLICATIONS

STN Database Descriptions, from 2006 Chemical Abstracts catalog, published 2006 by Chemical Abstracts Service, p. 52.*
Silverman, R. The Organic Chemistry of Drug Design and Drug Action, Chapter 2 "Drug Discovery, Design, and Development", published 1992 by Academic Press, pp. 4-47.*

* cited by examiner

*Primary Examiner*—Shaojia Anna Jiang
*Assistant Examiner*—Eric S Olson
(74) *Attorney, Agent, or Firm*—Francis Law Group

(57) ABSTRACT

The invention comprises a gastric device having an outer region and a gas producing material. The gastric device hydrates within a patient's stomach and the gas producing material expands the device to a greater volume. Accordingly, the volume of the hydrated, expanded gastric devices occupy space in the stomach cavity and reduce the amount of food the patient will ingest before reaching the feeling of fullness. Preferably, the gastric device is made from food grade materials. The gastric device is configured to expand to a desired volume and then degrade after a residence time, allowing the device to be passed by the patient's normal digestive process.

17 Claims, 5 Drawing Sheets

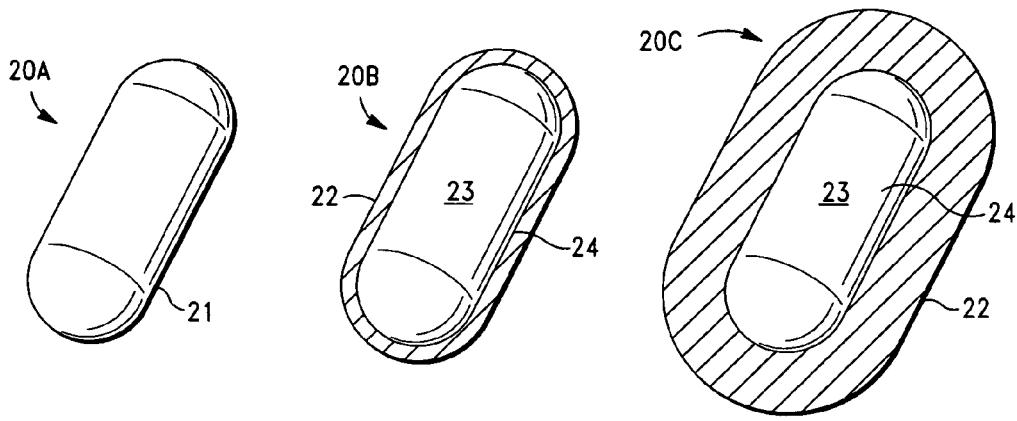
*FIG.-3A*  *FIG.-3B*  *FIG.-4*
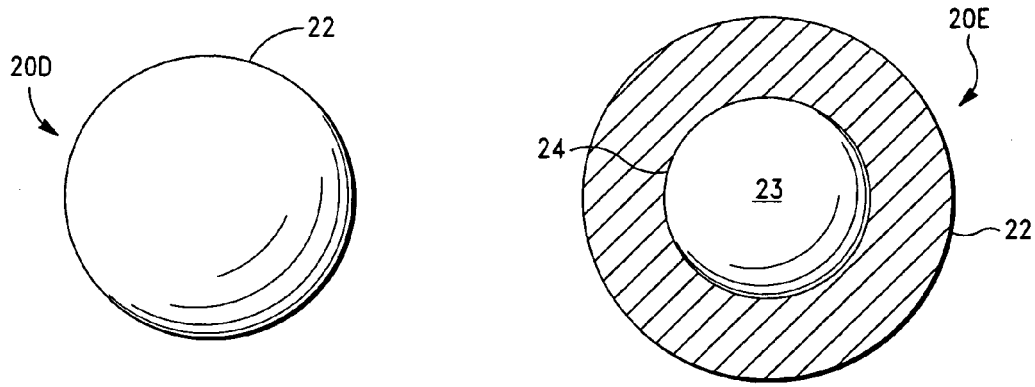
*FIG.-5A*  *FIG.-5B*
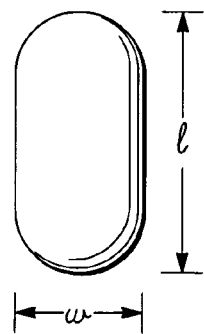  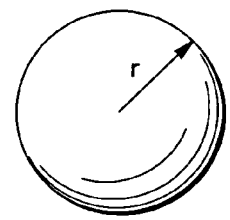
*FIG.-6*  *FIG.-7*

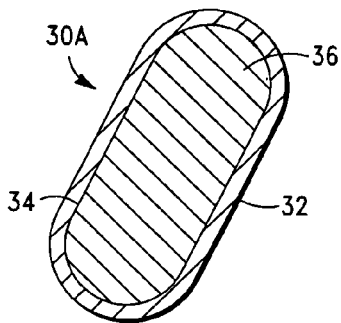
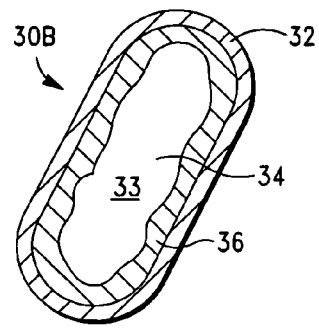
*FIG.–9A*  *FIG.–9B*
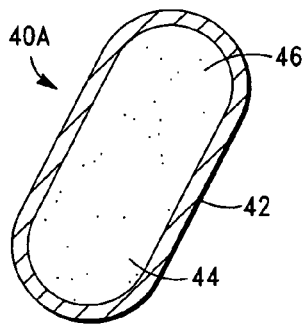
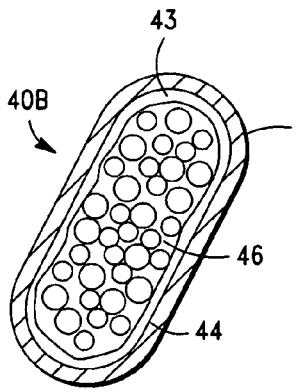
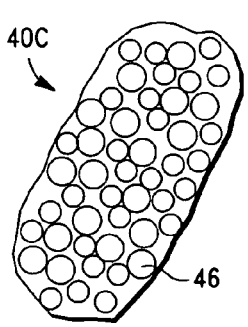
*FIG.–10A*  *FIG.–10B*  *FIG.–10C*
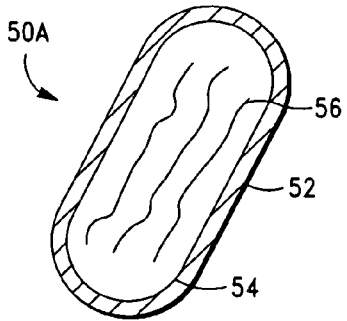
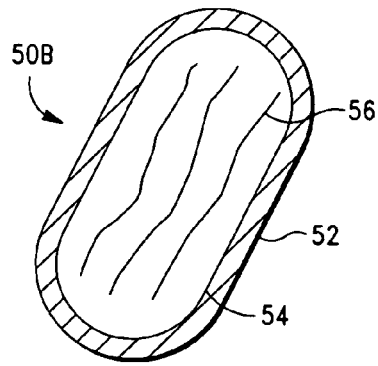
*FIG.–11A*  *FIG.–11B*

METHOD AND SYSTEM FOR TREATMENT OF EATING DISORDERS

FIELD OF THE PRESENT INVENTION

The present invention relates generally to the treatment of eating and gastrointestinal disorders. More particularly, the invention relates to an expandable gastric device that can reside in the stomach for a controlled and prolonged period of time.

BACKGROUND OF THE INVENTION

According to the American Medical Association, obesity is reaching epidemic proportions, affecting over 30% of American adults, or almost 70 million people. The percentage of affected adults (and children) is also climbing. In addition to the health risks presented by obesity itself, obesity increases the likelihood of a wide range of significant co-morbid health risks including cardiovascular complications (such as hypertension and hyperlipidemia), diabetes, gallbladder disease, cancer, polycystic ovary disease, pregnancy-related problems, arthritis-related problems and other orthopedic complications caused by stress on body joints.

Obesity can have several causes. Genetic, environmental and psychological factors are all believed to play a role in obesity. The mechanism for weight gain includes impaired metabolism of adipose tissue, physical inactivity (due to lifestyle or other illness), and uncontrolled appetite. Some illnesses, such as hypothyroidism, Cushing's disease and depression can also lead to obesity partly through hormonal effects, and partly through changes in appetite and lifestyle.

Regarding hormonal effects on obesity, the control of thyroid hormone secretion and adrenal gland secretion is at the level of the hypothalamus and pituitary regions of the brain. The hypothalamus secretes thyroid releasing factor which leads to release of thyroid stimulation hormone from the pituitary gland leading to increases in thyroid hormone production and release from the thyroid gland. In a similar fashion Corticotrophin releasing factor released from the hypothalamus leads to release of adrenocorticotrophic hormone that causes increased cortisol secretion from the adrenal glands causing Cushing disease.

Obesity can further be caused by certain drugs, such as steroids and some antidepressants. These effects are also thought to occur in the appetite centers in the brain.

Obesity is a common feature of neurologic diseases that appear to affect the appetite control center in the hypothalamic, pituitary and brain stem regions of the brain. Kline-Levine syndrome and sarcoidosis of the hypothalamus, for example, are associated with massive obesity.

When diet therapy proves ineffective, morbid obesity is often treated through bariatric surgery. Common bariatric surgical procedures include adjustable gastric banding and vertical banded gastroplasty (VBG).

In the noted surgical procedures, a band is surgically placed around the upper part of the stomach creating a small pouch. The pouch fills quickly when eating or drinking giving the patient the sensation of satiety.

Another popular treatment is the Roux-en-Y gastric bypass, in which a small stomach pouch is created and a section of the small intestine is attached to the pouch to allow food to bypass the lower stomach, the duodenum, and the first portion of the jejunum. This bypass reduces the amount of calories and nutrients the body absorbs.

It is also known to surgically insert a gastric balloon into the stomach to assume a portion of the volume of the stomach cavity, and, hence, reduce the available capacity of the stomach for food. This has the effect of reducing appetite and, consequently, over time (e.g., 3 months), and in combination with a suitable diet, causes weight loss.

Intragastric balloons, such as the device disclosed in U.S. Pat. No. 5,084,061, are typically designed to provide short-term therapy for moderately obese individuals requiring a reduction in weight prior to surgery, or as part of a dietary or behavioral modification program. Such devices are typically inserted into the stomach cavity in an outpatient setting (i.e., under endoscopic control), using local anesthesia and sedation.

After placement, the balloons are filled with saline solution or air from outside the cavity. Placement is typically for a period from 6 to 12 months. Removal of the balloons generally requires endoscopy.

A number of gastric balloon systems have also been employed that permit the volume of a gastric balloon to be varied over time. The purpose of facilitating volumetric changes in the gastric balloon is to provide periods of feelings of relief and well-being to the patient; not to prevent balloon accommodation and maintain appetite reduction. One such system is disclosed in U.S. Pat. No. 4,133,315 to Berman, which utilizes a flexible filling/release tube permanently coupled to the balloon. An even more invasive, surgically implanted tube design is described in U.S. Pat. No. 5,234,454 to Bangs.

In U.S. Pat. No. 5,084,061, a free floating gastric balloon is disclosed that includes a valve that can be detachable coupled to a filling tube. The device requires a physician's care and sedation for adjustment.

In addition to undesirable system complexity, each of the above-described bariatric procedures has associated risks. A significant concern with banded surgeries is a high incidence of complications, such as bleeding and/or obstruction. Though generally better tolerated than banded procedures, the Roux-en-Y gastric bypass still results in significant complications, such as vitamin and mineral deficiencies, and may lead to osteoporosis in the long-term.

Additionally, while any surgical procedure involves risks, surgical procedures on obese patients present significantly higher risks of complications and death. The obesity makes it difficult to administer anesthesia in proper doses. The surgical wounds often do not heal properly. Obese patients also face a higher risk of complications after surgery, such as deep venous thrombosis.

Severe weight loss and abnormal loss of appetite is also an equally serious condition that can lead to suffering and death. The most common example is anorexia nervosa, a condition that classically affects young women and is associated with pathologic alterations of hypothalamic and pituitary gland function. Severe anorexia can also occur in bowel conditions that cause early satiety (a feeling of fullness) or pain on eating. While anorexia is treatable with behavioral modifications, most patients require psychotropic drugs that appear effective in increasing appetite.

It would thus be desirable to provide a low-risk, unobtrusive and noninvasive method and system for treatment of eating disorders that readily prevents stomach distention and/or alternatively allows for simple, frequent and timely adjustments of the stomach cavity that is available for food intake.

It is therefore an object of the present invention to provide a method and system for treatment of eating disorders that is low-risk, unobtrusive and noninvasive.

It is another object of the invention to provide an expandable gastric device that substantially reduces or eliminates passage through the pyloric sphincter when inflated.

It is another object of the invention to provide a readily ingestible (i.e., easy to swallow) gastric device, which, when expanded, reduces the amount of food ingested to reach a feeling of fullness.

It is another object of the invention to provide an expandable, directive gastric device that is ingestible and allows food to pass through the stomach when inflated.

It is another object of the invention to provide an ingestible, inflatable gastric device having a controlled rate of inflation and, hence, expansion.

It is another object of the invention to provide an expandable, inflatable gastric device that is readily degradable (or dissoluble) by stomach contents and/or gastric fluid.

It is another object of the invention to provide an expandable, inflatable gastric device that is readily degradable (or digestible) by intestinal contents in the small and/or large intestines.

It is another object of the invention to provide an ingestible, expandable gastric device having a controlled rate of degradation.

SUMMARY OF THE INVENTION

In accordance with the above objects and those that will be mentioned and will become apparent below, the gastric device, in accordance with this invention generally comprises an outer region defining a first volume and a gas producing material wherein the gastric device increases to a second volume greater than the first volume and wherein the outer region defines a cavity containing gas produced by the gas producing material upon hydration of the gastric device. Preferably, the outer region further includes a hydration modifying material.

In one embodiment of the invention, the gastric device has an oblong configuration with a length in the range of approximately 2-15 cm and width in the range of approximately 0.4-6 cm. More preferably, the length is in the range of approximately 3-8 cm and the width is in the range of approximately 0.8-2 cm.

In another embodiment of the invention, the gastric device has a circular configuration with a radius in the range of approximately 0.25-6 cm.

According to the invention, the second volume is preferably sufficient to restrict entry into the lower gastric sphincter to the duodenum of a patient.

In one embodiment of the invention, the gastric device is configured to hydrate after contact with an aqueous material for a period of time in the range of approximately 1-30 min, and more preferably, in the range of approximately 5-10 min.

In one embodiment of the invention, the gastric device is configured to hydrate to approximately 50% after contact with an aqueous material for a period of time in the range of approximately 5 min.-3 hrs., and more preferably, in the range of approximately 10 min.-30 min.

In a further embodiment of the invention, the gastric device is configured to hydrate substantially completely after contact with an aqueous material for a period of time in the range of approximately 1 min.-4 hrs. Preferably, the gastric device is configured to hydrate substantially completely after contact with the aqueous material for a period of time less than approximately 3 hrs.

According to the invention, the outer region is configured to degrade after a first period of time to allow the gastric device to enter a patient's duodenum. The first period of time is preferably in the range of approximately 2 hr.-1 year, and more preferably, in the range of approximately 1 week-3 months.

In one embodiment of the invention, the gastric device is adapted to be directed to a desired point in a patient's stomach.

In a further embodiment of the invention, the gastric device expands to a second volume in the range of approximately 3-30 times greater than the first volume. Preferably, the second volume is in the range of approximately 10-20 times greater than the first volume.

In one embodiment of the invention, the gas producing material comprises a base. Preferably, the base is selected from the group consisting of sodium bicarbonate, sodium carbonate, hydrogen carbonates, alkali metals carbonates, organic cations, and sodium azide. More preferably, the base comprises sodium bicarbonate.

The gastric device can also include an acid. Preferably, the acid is selected from the group consisting of ascorbic acid, citric acid, fumaric acid, oxalic acid, succinic acid, tartaric acid, maleic acid, and phosphoric acid/dihydrogen phosphate mixtures. More preferably, the acid comprises citric acid.

In the above-noted embodiments, the acid and the base preferably comprise solid particles having a protective coating.

In one embodiment of the invention, the outer region comprises a hydrophilic gel-forming agent. Preferably, the gel-forming agent is selected from the group consisting of acacia (gum Arabic), agar, agarose, alginate gels, alginic acid, alginate gums, amylopectin, arbinoglactan, carob bean gum, carrageenan, chondroitin sulfate, eucheuma, fucoidan, furcellaran, gelatin, gellan, guar gum, gum ghatti, gum karaya, hypnea, karaya, laminaran, locust bean gum, natural gum, pectins, starches, polypeptides, polyamino acids, tragacanth, xanthan, psyllium, and maltodextrin, like materials and mixtures thereof.

In another embodiment of the invention, the gas producing material comprises a gel-forming agent. Preferably, the gel-forming agent is selected from the group consisting of acacia (gum Arabic), agar, agarose, alginate gels, alginic acid, alginate gums, amylopectin, arbinoglactan, carob bean gum, carrageenan, chondroitin sulfate, eucheuma, fucoidan, furcellaran, gelatin, gellan, guar gum, gum ghatti, gum karaya, hypnea, karaya, laminaran, locust bean gum, natural gum, pectins, polypeptides, polyamino acids, tragacanth, xanthan, like materials and mixtures thereof.

More preferably, the gel-forming agent is selected from the group consisting of agar and carrageenan.

In the above-noted embodiments, the gastric device can further include a base and an acid.

In one embodiment of the invention, the outer region includes reinforcing fibers. The reinforcing fibers can comprise soluble reinforcing fibers, preferably selected from the group consisting of polysaccharide gums, including, without limitation, carboxymethyl cellulose, methocel, carrageenan, guar gum, alginate gels, pectins, xanthan, gum Arabic (acacia), gum tragacanth, karaya, agar, gellan, alpha-polyhydroxy acids, polyglycolide (PGA), poly(L-lactide), poly(D,L-lactide), poly(.epsilon.-caprolactone), poly(trimethylene carbonate), poly(ethylene oxide) (PEO), poly(.beta.hydroxybutyrate) (PHB), poly(.beta.-hydroxyvalerate) (PHVA), poly(p-dioxanone) (PDS), poly(ortho esters), tyrosine-derived polycarbonates, like materials and mixtures thereof.

Alternatively, the reinforcing fibers can comprise insoluble fibers, preferably selected from the group consisting of insoluble polysaccharides, cellulose, phenylpropane molecules polymers, lignin, bast fibers, Kozo, Gampi, grasses, kenaf, bagasse, jute, hemp, flax, like materials and mixtures thereof.

Preferably, the reinforcing fibers have a length in the range of approximately 0.1 mm-12 cm. More preferably, the reinforcing fibers have a length in the range of approximately 0.3-10 mm.

In one embodiment of the invention, the outer region is sealed with a gum material. In a further embodiment, the outer region is sealed with high gel strength agar.

In accordance with one embodiment of the invention, the outer region of the gastric device comprises agar reinforced with cellulose fibers and coated with carrageenan.

In another aspect of the invention, the gastric device has an outer region comprising agar having a thickness in the range of approximately 0.1-0.3 mm.

In yet another embodiment of the invention, the gastric device has an outer region that comprises a water permeable hydrophilic, gas-impermeable membrane. Preferably, the membrane is regenerated cellulose dialysis tubing.

In a further embodiment of the invention, the gastric device includes an agent selected from the group consisting of an expansion agent, a therapeutic agent, a weight reduction agent and an appetite suppressant.

In one embodiment of the invention, the gastric device is substantially solid before hydration.

In another embodiment of the invention, before the gastric device is exposed to an aqueous material, the outer region of the gastric device defines a cavity containing the gas producing material.

In one embodiment, the gas producing material comprises a high viscosity foam. Preferably, the high viscosity foam is selected from the group consisting of polypeptides proteins, egg white, and albumin. The high viscosity foam can further include a gel-forming agent.

In one embodiment of the invention, the high viscosity foam further includes a base. In a further embodiment, the high viscosity foam has alternating layers of acid and base.

According to one embodiment of the invention, the gastric device has foamed agar and egg white gas producing material and a high gel strength agar outer region reinforced with cellulose fibers. Preferably, the gastric device is sealed with a layer of carrageenan.

In another embodiment of the invention, the gas producing material comprises a gas producing member configured to release gas and expand upon hydration. Preferably, the gas producing member comprises a sheet of material that forms a gas when hydrated and is degradable by gastric acid.

In the noted embodiments, the sheet can be compressed prior to hydration, such as by folding or rolling.

In a presently preferred embodiment, the sheet comprises preformed and dried agar gel. Preferably, the sheet is overcoated with a layer of sodium bicarbonate-containing agar film. Also preferably, the outer region is a high gel-strength agar having cellulose reinforcing fibers.

In another embodiment, the outer region and the sheet comprise closed pore foam.

In the noted embodiments, the gastric device is configured to degrade after a first period of time to allow the gastric device to enter a patient's duodenum. Preferably, the first period of time is in the range of approximately 2 hrs-2 months. More preferably, the first period of time is in the range of approximately 1-7 days.

The invention also includes a method for treating a patient having an eating disorder, wherein the method comprises the steps of i) providing a gastric device having an outer region defining a first volume and a gas producing material and ii) ingesting the gastric device to position the gastric device within the patient's stomach, whereby the gastric device hydrates with an aqueous material in the patient's stomach to produce gas and whereby the gastric device expands to a second volume greater than the first volume. Preferably, the second volume is sufficient to restrict entry of the gastric device into the duodenum of a patient.

In one embodiment, the gastric device hydrates to approximately 50% after contact with the aqueous material for a period of time in the range of approximately 5 min.-3 hrs. Preferably, the period of time is in the range of approximately 10-30 min.

In another embodiment of the invention, the gastric device hydrates substantially completely after contact with the aqueous material for a period of time in the range of approximately 1 min.-4 hrs. Preferably, the period of time is less than approximately 3 hrs.

In one embodiment of the invention, the gastric device degrades after a first period of time to allow the gastric device to enter the patient's duodenum. Preferably, the first period of time is in the range of approximately 2 hr.-1 year, and more preferably, in the range of approximately 1 week-3 months.

In one embodiment of the invention, the second volume to which the gastric device expands is in the range of approximately 3-30 times greater than the first volume. Preferably, the second volume is in the range of approximately 10-20 times greater than the first volume.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 3A is a perspective view of one embodiment of a gastric device, according to the invention;

FIG. 3B is a perspective, sectional view of the gastric device shown in FIG. 3A after hydration and expansion, according to the invention;

FIG. 4 is a perspective, sectional view of another embodiment of a gastric device after hydration and expansion, according to the invention;

FIG. 5A is a plan view of another embodiment of a gastric device, according to the invention;

FIG. 5B is a plan, sectional view of the gastric device shown in FIG. 5A after hydration and expansion, according to the invention;

FIGS. 6 and 7 are schematic illustrations of oblong and spherical shaped gastric devices, according to the invention;

FIG. 9A is a perspective, sectional view of another embodiment of a gastric device, according to the invention;

FIG. 9B is a perspective, sectional view of the gastric device shown in FIG. 9A after hydration and expansion, according to the invention;

FIG. 10A is perspective, sectional view of yet another embodiment of a gastric device, according to the invention;

FIG. 10B is a perspective, sectional view of the gastric device shown in FIG. 10A after hydration and expansion, according to the invention;

FIG. 10C is a perspective, sectional view of the gastric device shown in FIG. 10A after complete hydration and degradation of the outer layer, according to the invention;

FIG. 11A is a perspective, sectional view of another embodiment of a gastric device, according to the invention; and FIG. 11B is a perspective, sectional view of the gastric device shown in FIG. 11A after hydration and expansion, according to the invention.

DETAILED DESCRIPTION OF THE INVENTION

Figure 1:
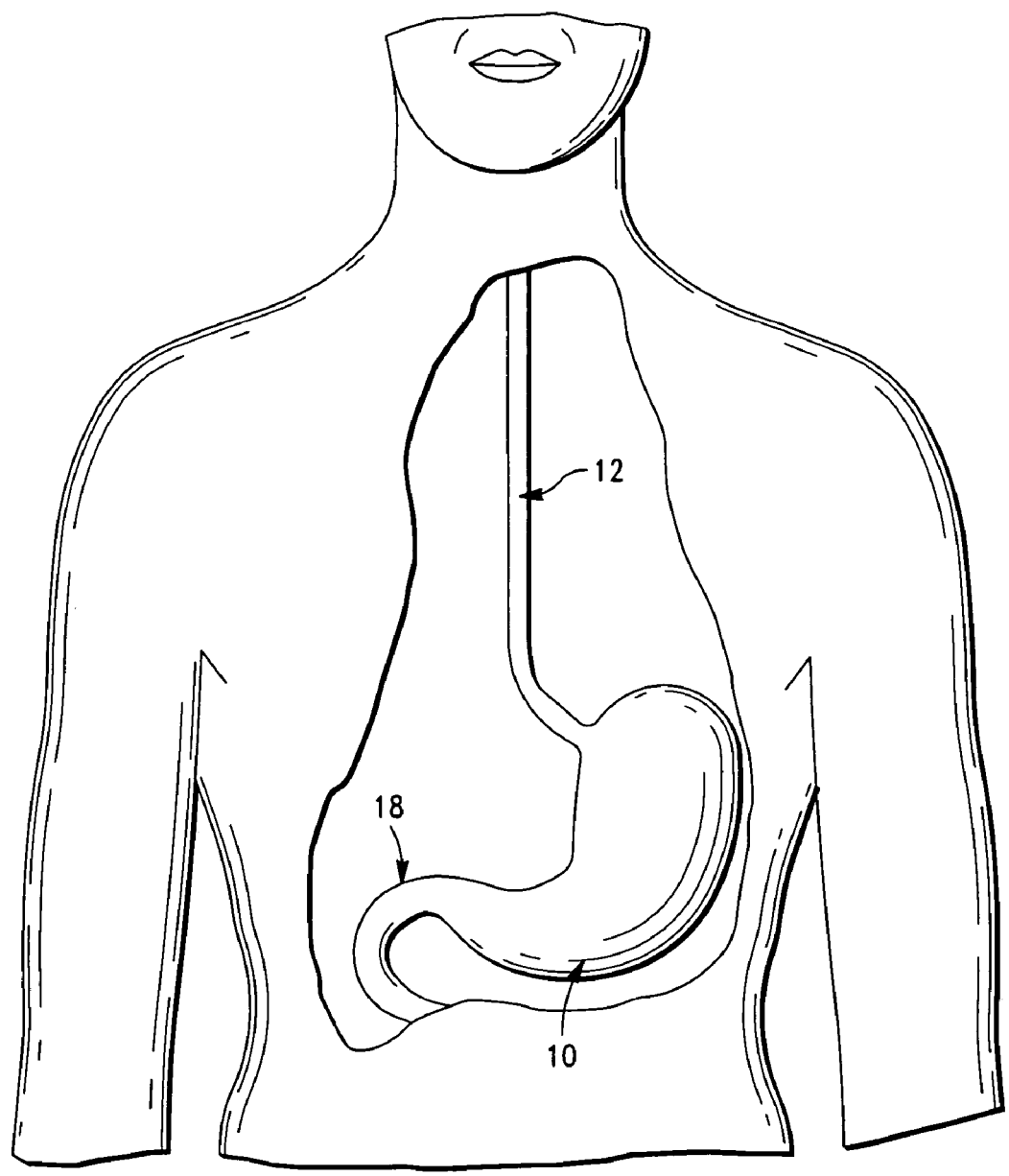
FIG. 1 is an illustration of a portion of the digestive system of a human subject.

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise. Thus, for example, reference to "a gastric device" includes two or more such devices; reference to "core material" includes two or more such materials and the like.

Definitions

The term "gastric device", as used herein, means a device having an internal cavity (e.g., balloon) that is formed to a size suitable for oral administration to a subject and, following administration, expands to a size greater than the administration size.

The terms "expandable" and "inflatable", as used herein, mean and include the ability to expand upon hydration. As discussed in detail herein, the expandable gastric devices of the invention include or have the capability of forming an internal cavity that is adapted to receive a gas released by a hydrated material (or materials), which is used to form the gastric device.

The term "food grade", as used herein, means and includes, a material that is commonly consumed as a food or employed as a food additive.

The term "directive", as used herein, means the ability to move in a desired direction or be placed in a desired location.

The term "gel-forming agent", as used herein, means a material that hydrates in water or in an aqueous environment, such as gastric fluid, and exhibits the ability to retain a significant fraction of water within its structure.

The term "viscosity building material", as used herein, means a material that hydrates in water or an aqueous environment, such as gastric fluid, and exhibits the ability to retain a significant fraction of formed gas. Viscosity building materials thus include, without limitation, gel-forming agents such as water soluble polymers, sodium and calcium polyacrylic acid, polyacrylic acid, polymethacrylic acid, polymethylvinylether co-maleic anhydride, polyvinylpyrrolidone, polyethylene oxide, hydroxypropyl cellulose, hydroxypropyl methyl cellulose, polyvinyl alcohol, hydroxyethyl cellulose, hydroxymethyl methacrylate, sodium carboxymethyl cellulose, calcium carboxymethyl cellulose, methyl cellulose, and natural substances, such as psyllium, maltodextrin, xanthan gum, tragacanth gum, agar, gellan gum, kayara gum, alginic acids, pectins, starch, copolymers and mixtures and blends thereof.

The term "foam", as used herein, means and includes any material that hydrates in water or an aqueous environment, such as gastric fluid, and maintains a significant fraction of water within its structure. The foam material is also capable of retaining a significant fraction of formed gas by maintaining at least one pore or opening.

The term "foam" thus includes, but is not limited to, natural gel-forming substances, either with or without further crosslinking, alone or in combination, acacia (gum Arabic), agar, agarose, alginate gels or alginic acid, including non-cross linked and cross linked alginate gums, wherein the cross linked alginate gums can be cross linked with di- or trivalent ions, amylopectin, arbinoglactan, carob bean gum, carrageenan, chondroitin sulfate, eucheuma, fucoidan, furcellaran, gelatin, gellan, guar gum, gum ghatti, gum karaya, hypnea, karaya, laminaran, locust bean gum, natural gum, pectins, polypeptides, polyamino acids, tragacanth, and xanthan, like materials, and combinations and mixtures thereof.

The "foams" of the invention can be obtained by blowing, beating, shaking, spraying or stirring a solution of polymer in the presence of the desired gas, such as air, while the gel is being formed. Natural or synthetic foam stabilizing agents can also be added, such as protein, egg white, or detergents, such as SDS.

The term "wet strength", as used herein, means the ability of a hydrated material to withstand grinding by the stomach structure(s).

As will be appreciated by one having ordinary skill in the art, the present invention substantially reduces or eliminates the disadvantages and shortcomings associated with prior art gastric devices. The invention generally comprises a gastric device that expands sufficiently in the stomach of a subject to at least partially suppress the subject's appetite. A key advantage of the gastric devices of the invention is the provision of a safe and efficient means of limiting food and, hence, caloric intake to facilitate weight reduction. The gastric devices are also readily adaptable to meet the needs of virtually any subject.

According to the invention, the gastric devices of the invention can be ingested in dry form with most ingestible fluids (e.g., water, juice, etc.) or food. The gastric devices are also robust, i.e., able to withstand grinding by the stomach muscles.

Figure 2:
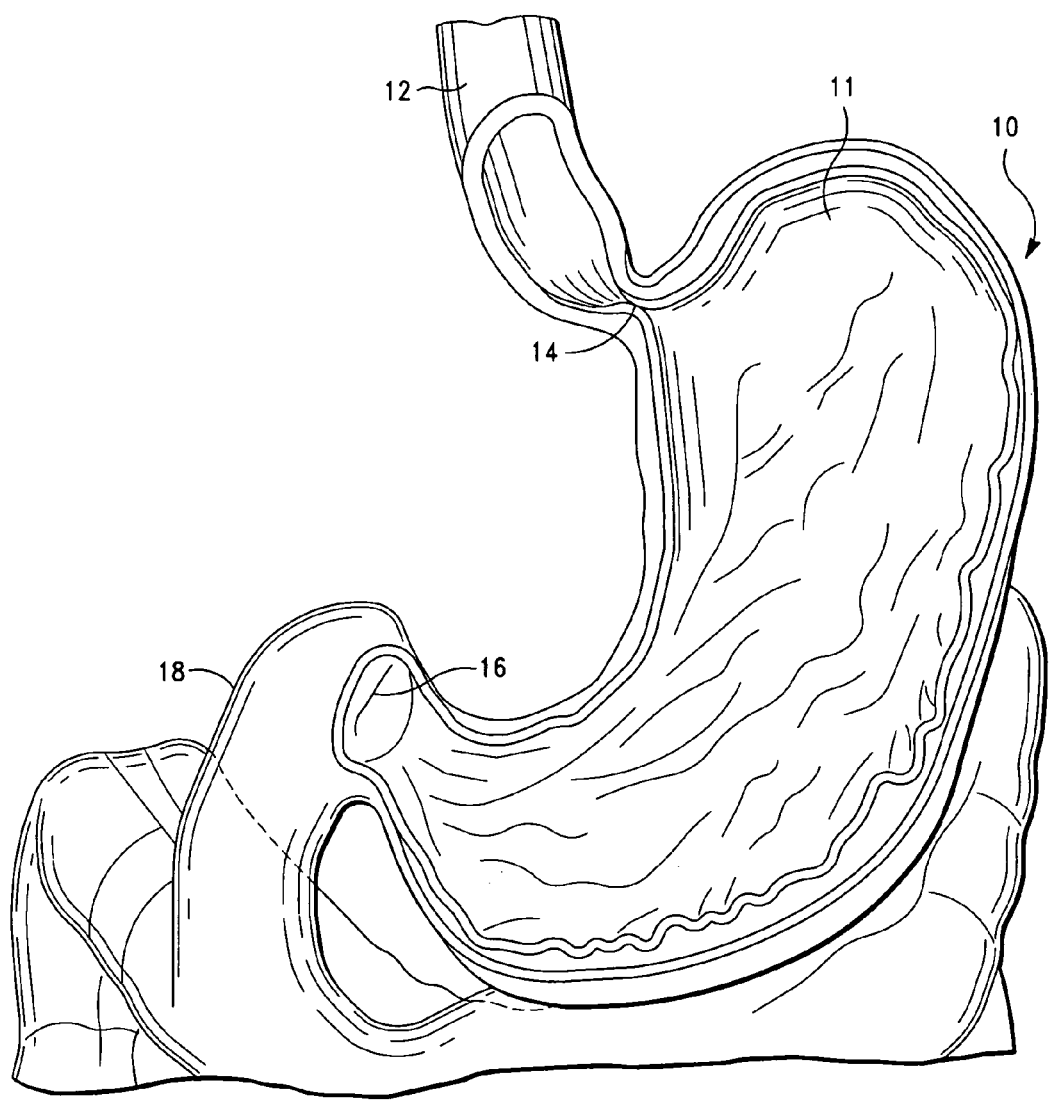
FIG. 2 is a partial section view of a portion of the digestive system.

Before describing the present invention in detail, it is believed that it will be useful to briefly review the anatomy of the stomach and esophagus. Referring to FIGS. 1 and 2, the esophagus 12 is a muscular tube that carries food from the throat to the stomach 10.

The top end of the esophagus 12 is the narrowest part of the entire digestive system and is encircled by a sphincter (i.e., circular muscle) that is normally closed, but opens to allow the passage of food. There is a similar sphincter (i.e., lower esophageal sphincter) 14 where the esophagus 12 enters the stomach 10.

The stomach 10 is a sac-like organ having a fundus 11 (i.e., expanded curvature region) and a lower pyloric sphincter 16, which controls passage of food from the stomach 10 to the duodenum 18 (i.e., first part of small intestine). In addition to holding food, the stomach 10 serves as a mixer and grinder of food. The stomach 10 also secretes acid and powerful enzymes that further break down the food to form a paste or liquid.

Referring now to FIGS. 3A and 3B, there is shown one embodiment of a gastric device of the invention. As illustrated in FIG. 3A, the gastric device 20A (prior to ingestion) initially has a substantially solid structure 21. Referring to FIG. 3B, after ingestion and hydration and, hence, gas formation, the device 20A forms device 20B, having an internal, expandable cavity 24 (with the released gas 23 contained therein) and an outer region (or shell) 22.

As discussed in detail herein, the outer region 22 can also comprise a separate material (or coating) that is adapted to delay degradation and, hence, hydration of the core material or modify the hydration and, hence, expansion rate. According to the invention, the gastric device 20A (as well as all gastric devices described herein) can comprise various sizes and virtually any shape (e.g., oblong, circular, cylindrical, cube etc).

In one embodiment of the invention, the gastric device (e.g., 20A) has a substantially oblong shape with a maximum length (l) in the range of approximately 2-15 cm, more preferably, in the range of approximately 3-8 cm, and a maximum width (w) in the range of 0.4-6 cm, more preferably, in the range of approximately 0.8-2 cm (see FIG. 6).

In another embodiment, the gastric device (e.g., 20C) is substantially round or circular in shape (see FIGS. 5A and 5B) and preferably (pre-hydration) has a radius in the range of approximately 0.25-6 cm (see FIG. 7). The round gastric devices can also have substantially flat top and bottom surfaces (i.e., pancake configuration).

As will be appreciated by one having ordinary skill in the art, the noted gastric device dimensions facilitate easy ingestion by a subject. The noted range of expanded gastric device dimensions also facilitates control of gastric retention.

As indicated above, according to the invention, upon entry into the stomach, the gastric devices 20A, 20D absorb the liquid contained in the stomach (e.g., ingested fluids, hydrochloric acid, etc.) and produce a gas 23 (e.g., $CO_2$) that is contained within the device cavity 24. As the gas 23 is released, the cavity and, hence, gastric device expands (see FIGS. 3B and 5B). Water alone or in combination with other stomach contents (e.g., acid) is used to direct and define the inflation and, hence, expansion of the gastric device.

As will be appreciated by one having ordinary skill in the art, the volume of the hydrated, expanded gastric devices of the invention will occupy space in the stomach cavity that is normally used for receipt of consumed substances (e.g., food, drink) and, hence, reduce the amount of food a subject will ingest before reaching the feeling of fullness.

Preferably, the gastric devices 20A, 20D (as well as all gastric devices described herein) expand to a size that prohibits the device from passing through the lower gastric sphincter into the duodenum (or, alternatively, allows for controllable time to passage) while allowing food to pass therethrough. According to the invention, when a gastric device enters into the duodenum, the device is readily degraded and/or passed in the small and large intestines. Blockage is thus substantially reduced or eliminated.

According to the invention, the on-set and rate of hydration of the gastric devices 20A, 20D is infinitely adjustable. Preferably, the gastric devices 20A, 20D have an initial delayed hydration period in the range of approximately 1 min.-30 min., more preferably, approximately 5 min.-10 min., to prevent the devices from expanding in the esophagus.

In a preferred embodiment of the invention, the gastric devices 20A, 20D have a partial hydration rate (i.e., approx. 50% hydration) in the range of approximately 5 min.-3 hrs., more preferably, in the range of approximately 10 min.-30 min. Even more preferably, the gastric devices reach full hydration (i.e., substantially complete expansion) in the range of approximately 1 min.-4 hrs., more preferably, within 3 hrs. after ingestion.

The materials (discussed below) and thickness of the outer region 22 (see, e.g., FIGS. 3B and 4) of the outer region 22 can also be selected to achieve a desired degradation or, alternatively, passage and/or degradation rate(s) and, hence, desired residence time (e.g., 2, 6, 9, 12 or 24 hours or more) in the stomach. Upon expiration of the predetermined residence time (i.e., degradation of the device or, alternatively, passage), the gastric device and/or device material simply passes into the intestines and through as a human fecal waste product.

Figure 8:
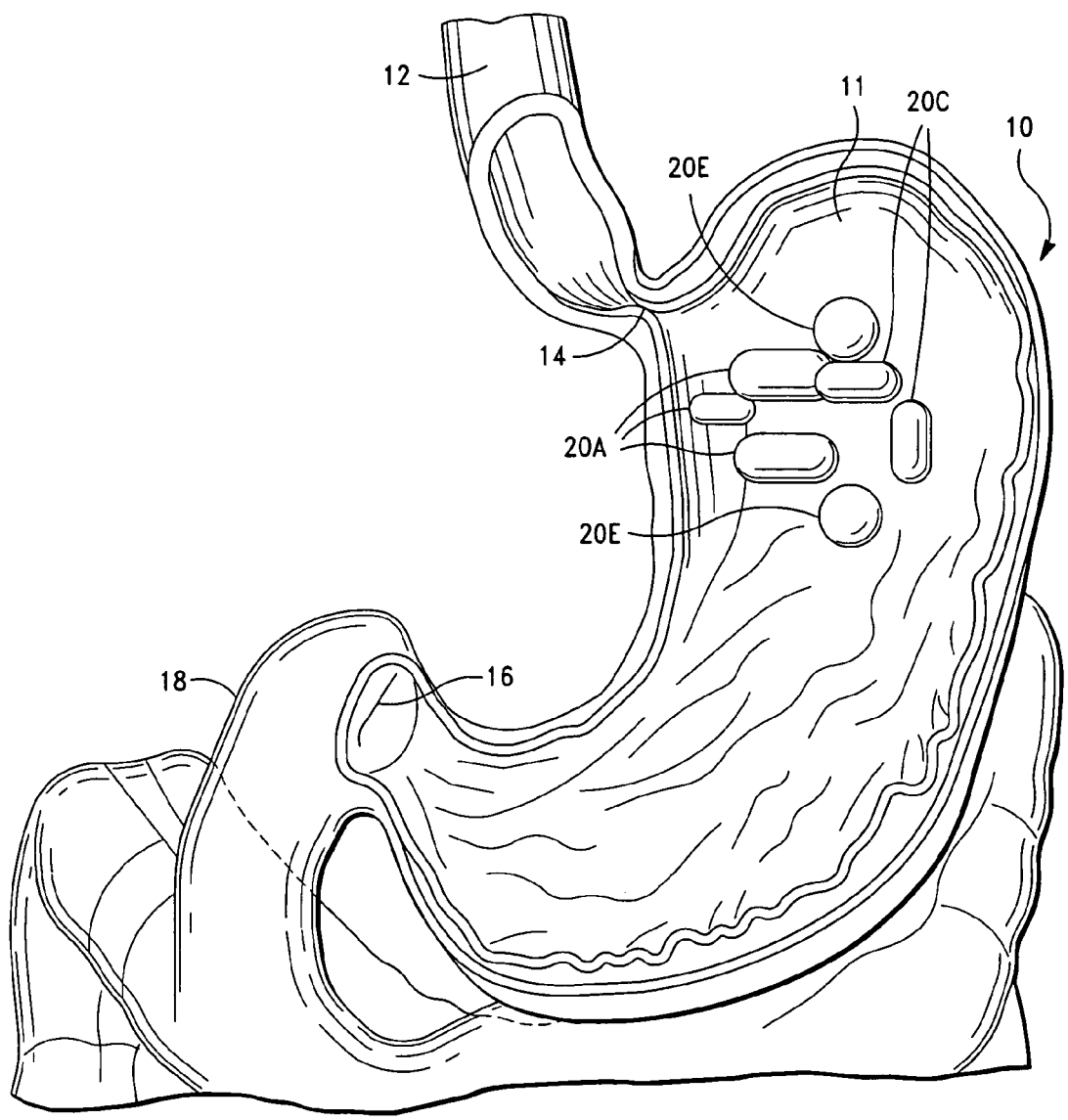
FIG. 8 is an illustration of a portion of the digestive system of the subject, showing placement of the gastric devices in the stomach cavity, according to the invention.

The gas filled gastric devices of the invention (including devices 20B, 20C and 20E) are also directive. As illustrated in FIG. 8, the devices are thus capable of being directed to a desired point in the stomach (e.g., proximate the fundus 11).

According to the invention, the gastric devices 20A, 20D are expandable (i.e., expansion coefficient) on hydration from approximately 3-30 fold or more. In a preferred embodiment of the invention, the gastric devices 20A, 20D have an expansion efficient in the range of approximately 10-20. The size of the gastric device 20A, 20D (and quantity ingested) can thus be tailored to suit a particular subject and/or weight reduction program.

In a preferred embodiment, the gastric devices 20A, 20D (as well as all gastric devices described herein) comprise "food grade" materials that form a gas when hydrated. By way of example, it is well known in the art that sodium bicarbonate, a preferred material, releases $CO_2$ when hydrated in the presence of an acid. As will thus be appreciated by one having ordinary skill in the art, various food grade materials can thus be employed within the scope of the invention.

In one embodiment of the invention, the gastric devices 20A, 20D include a base and an acid. Suitable bases include, without limitation, sodium bicarbonate, sodium carbonate, hydrogen carbonates or carbonates of alkali metals or organic cations, such as ammonium derivatives and sodium azide, and combinations and mixtures thereof.

In a preferred embodiment of the invention, the base comprises sodium bicarbonate. Sodium bicarbonate is preferable over sodium carbonate, since only one-half of the acid is required for gas release.

Suitable acids, include, without limitation, citric acid, ascorbic acid, ascorbic acid, fumaric acid, oxalic acid, succinic acid, tartaric acid, maleic acid and inorganic acids, such as phosphoric acid/dihydrogen phosphate mixtures, like acids and mixtures thereof. In a preferred embodiment, the acid comprises citric acid.

According to the invention, solid particles of the aforementioned bases and acids can also be coated with a thin protective layer, such as a hydrophilic, gel-forming agent (listed below), to maintain their functional integrity during storage.

In another embodiment of the invention, the gastric devices 20A, 20D comprise a hydrophilic gel-forming agent. Suitable gel-forming agents include, without limitation, natural gel-forming substances, either with or without further crosslinking, alone or in combination, acacia (gum Arabic), agar, agarose, alginate gels or alginic acid, including non-cross linked and cross linked alginate gums, wherein the cross linked alginate gums can be cross linked with di- or trivalent ions, amylopectin, arbinoglactan, carob bean gum, carrageenan, chondroitin sulfate, eucheuma, fucoidan, furcellaran, gelatin, gellan, guar gum, gum ghatti, gum karaya, hypnea, karaya, laminaran, locust bean gum, natural gum, pectins, polypeptides, polyamino acids, tragacanth, and xanthan, like materials, and combinations and mixtures thereof.

Natural food grade materials (or substances), such as agar and carrageenan, are preferred by virtue of their stability in an acidic environment and established intestinal degradability.

In an alternative embodiment of the invention, the gastric devices 20A, 20D comprise at least one of the aforementioned gel-forming agents, and a base and acid.

In additional embodiments of the invention, the gastric devices 20A, 20D comprise a material selected from the group consisting of water permeable hydrophilic, but gas-impermeable preformed materials, such as membranes that are widely used for dialysis, including kidney dialysis or alternatively for molecular filtration, water purification, osmosis, ultrafiltration, nanofiltration, microfiltration etc. Pore sizes can range from a molecular weight cutoff of 1,000 to pore size diameters of 10 micrometer. For exclusion of larger molecules, such as pepsin, it is preferable to use low cutoffs such as 2,000 to 10,000, whereas for rapid fluid exchange a large pore size diameter of 0.8 to 3 micrometer is preferred. Regenerated cellulose dialysis tubing, obtainable from Spectra/Por, is a preferred material.

According to the invention, the gastric devices 20A, 20D can further include other materials or agents, such as an expansion agent, therapeutic agent, weight reduction agent and/or appetite suppressant. The gastric devices 20A, 20D can also include enzymes that aid in the degradation of the outer region 22 following ingestion of the device. The noted materials and agents are hereinafter referred to as "supplemental agents."

Referring now to FIGS. 9A and 9B, there is shown another embodiment of a gastric device of the invention. Referring first to FIG. 9A, there is shown the gastric device 30A prior to ingestion. As illustrated in FIG. 9A, the gastric device 30A includes an outer region or layer 32, an internal cavity 34 and a gas producing material 36 disposed therein.

According to the invention, the gastric device 30A can similarly comprise a multitude of sizes and shapes (e.g., oblong, spherical, etc.). The gastric device 30A preferably has dimensions similar to gastric devices 20A, 20D.

Referring now to FIG. 9B, there is shown an illustration of the device 30A after ingestion and hydration in the stomach (designated generally "30 B"). As illustrated in FIG. 9B, when hydrated, the gas producing core material 36 degrades and releases a gas 33. The gas 33 fills and inflates the cavity 24, forming expanded device 30B.

According to the invention, the outer layer 32 can similarly comprise various food grade materials that are degradable (or erodible) by gastric fluid or intestinal contents. Suitable materials that can be employed to form the outer layer 32 thus include, without limitation, natural gel-forming substances, either with or without further crosslinking, alone or in combination, acacia (gum Arabic), agar, agarose, alginate gels or alginic acid, including non-cross linked and cross linked alginate gums, wherein the cross linked alginate gums can be cross linked with di- or trivalent ions, amylopectin, arbinoglactan, carob bean gum, carrageenan, chondroitin sulfate, eucheuma, fucoidan, furcellaran, gelatin, gellan, guar gum, gum ghatti, gum karaya, hypnea, karaya, laminaran, locust bean gum, natural gum, pectins, polypeptides, polyamino acids, tragacanth and xanthan, like materials, and combinations and mixtures thereof. Preferred gelling materials for the outer layer 32 are digestible natural substances, such as food grade agar and carrageenan.

According to the invention, the outer layer 32 can also include reinforcing fibers to enhance the structural integrity of the gastric device 30A. Suitable reinforcing fibers include, without limitation, soluble fibers and insoluble fibers.

Preferably, the soluble reinforcing fibers are selected from the group consisting of polysaccharide gums, including, without limitation, carboxymethyl cellulose, methocel, carrageenan, guar gum, alginate gels, pectins, xanthan, gum Arabic (acacia), gum tragacanth, karaya, agar, gellan, and like materials, and biodegradable polymers, including, without limitation, alpha-polyhydroxy acids, polyglycolide (PGA), poly(L-lactide), poly(D,L-lactide), poly(.epsilon.-caprolactone), poly(trimethylene carbonate), poly(ethylene oxide) (PEO), poly(.beta.hydroxybutyrate) (PHB), poly(.beta.-hydroxyvalerate) (PHVA), poly(p-dioxanone) (PDS), poly (ortho esters), tyrosine-derived polycarbonates, and polypeptides and copolymers of the above.

Additional biodegradable polymers, which can be employed within the scope of the present invention, are set forth in U.S. Pat. Nos. 6,858,222, 6,272,258, 6,596,296 and 4,147,779; the disclosures of which are expressly incorporated by reference herein.

Preferably, the insoluble reinforcing fibers are selected from the group consisting of insoluble polysaccharides, including, without limitation, cellulose and polymers of phenylpropane molecules (e.g., lignin), bast fibers, Kozo or Gampi. Additional fiber sources include grasses, kenaf, bagasse, jute, hemp and flax.

Preferably, the reinforcing fibers have a length in the range of approximately 0.1 mm to 12 cm, more preferably, in the range of approximately 0.3-10 mm.

The outer layer 32 can also be sealed with a gum material, such as high gel strength agar. As will be appreciated by one having ordinary skill in the art, the high gel strength agar provides additional wear resistance. The additional outer layer or coating will also substantially reduce or eliminate any pinholes through which the trapped gas might escape.

In a preferred embodiment of the invention, the outer layer 32 comprises agar reinforced with cellulose fibers, which is coated with carrageenan.

According to the invention, the thickness of the outer layer 32 and/or material employed to form same can similarly be selected control to the on-set and rate of degradation and, hence, hydration of the core material 36. By way of example, in one embodiment of the invention, the outer layer 32 is formed from agar and has a thickness in the range of approximately 0.1-0.3 mm. Depending on the materials contained in the subject's stomach (e.g., water content, chemistry, pH, etc), the noted device would (on average) commence hydration within 10 min. after ingestion and preferably reach substantially full hydration and, hence, expansion within 3 hrs.

Residence time of the device 30A in the stomach is also similarly adjustable. According to the invention, residence time can range from less than one hour to days, weeks, or more.

The core material 36 can similarly comprise one of the aforementioned "food grade" materials and/or combinations thereof. Preferably, the core material 36 comprises a natural gel-forming substance, either with or without further crosslinking, alone or in combination, acacia (gum Arabic), agar, agarose, alginate gels or alginic acid, including non-cross linked and cross linked alginate gums, wherein the cross linked alginate gums can be cross linked with di-or trivalent ions, amylopectin, arbinoglactan, carob bean gum, carrageenan, chondroitin sulfate, eucheuma, fucoidan, furcellaran, gelatin, gellan, guar gum, gum ghatti, gum karaya, hypnea, karaya, laminaran, locust bean gum, natural gum, pectins, polypeptides, polyamino acids, tragacanth, xanthan, like materials, copolymers of the above, and combinations and mixtures thereof. Naturally occurring substances, especially those designated as food or food additives, are preferred.

The core material 36 and/or outer layer 32 can also include a viscosity building material and any of the aforementioned supplemental materials (e.g., weight reduction agent, appetite suppressant, etc.).

According to the invention, the core material 36 and/or outer layer 32 can solely comprise a viscosity building material.

In a preferred embodiment, the core material 36 comprises carrageenan, a foam gel, sodium bicarbonate and citric acid, and the outer layer 32 comprises cellulose fiber reinforced agar gel.

Preferably, the gastric device 30A also has a delayed hydration period in the range of approximately 5 min.-30 min., more preferably, in the range of approximately 5 min.-10 min. and an expansion coefficient in the range of approximately 10-20 min. The device 30A also preferably achieves substantially complete hydration in the range of approximately 30 min.-3 hrs., more preferably, in the range of approximately 10 min.-30 min. Even more preferably, the gastric device 30A reaches substantially full hydration and, hence, substantially complete expansion in approximately 1 hr.

The gastric device 30A also has an adjustable residence time (e.g., hours, days, weeks, etc.). In a preferred embodiment, the residence time is in the range of approximately 2 hr.-1 year, more preferably, in the range of approximately 1 week to three 3 months.

Referring now to FIGS. 10A-10C, there is shown yet another embodiment of a gastric device of the invention. Referring first to FIG. 10A, there is shown the gastric device 40A prior to ingestion. As illustrated in FIG. 10A, the gastric device 40A includes an outer region or layer 42, an internal cavity 44 and a gas producing foam 46 disposed therein.

According to the invention, the gastric device 40A can similarly comprise a multitude of sizes and shapes. The gastric device 40A also preferably has dimensions similar to gastric devices 20A, 20D.

Referring now to FIG. 10B, there is shown an illustration of the device 40A after ingestion and hydration in the stomach (designated generally "40 B"). As illustrated in FIG. 10B, when hydrated, the gas producing foam 46 expands and releases a gas 43. The expanded foam 46 and gas 43 fill and inflate the cavity 24, forming expanded device 40B.

According to the invention, gas production can be designed to occur inside the foam on rehydrating (inside the stomach) by soaking the preformed and dried foam in a solution of sodium bicarbonate and by drying the foam thereafter. The acid required for reaction with the base can be provided from stomach juice or, alternatively, can be present by maintaining a short physical distance between acid and base components. This can be achieved by layering (in alternating fashion) acid and base containing foam sheets. Acid, such as citric acid, containing foam can be formed at once or by soaking a citric acid solution into preformed foam.

Referring now to FIG. 10C, there is shown an illustration of the device 40B after further hydration and total degradation of the outer layer 42. As illustrated in FIG. 10C, after the outer layer 42 is degraded, the device (designated generally "40C") comprises the expanded foam 46. The device 40C (i.e., expanded foam) preferably remains substantially intact until degraded by the gastric fluid(s).

According to the invention, the outer layer 42 similarly can comprise various, food grade materials that are degradable (or erodible) by gastric fluid, such as the aforementioned outer layer 32 materials. Suitable materials that can be employed to form the outer layer 42 thus include, without limitation, proteinaceous materials or acid unstable polymers in combination with agar, xanthan, locust bean gums, carrageenan, and combinations and mixtures thereof.

According to the invention, the outer layer 42 can similarly include one of the aforementioned reinforcing fibers. The outer layer 42 can also be coated with an additional layer of degradable material, such as the aforementioned outer layer 42 materials. The outer layer 42 can also be sealed with a gum material, such as high gel strength agar.

The outer layer 42 can also include a viscosity building material and/or any of the aforementioned supplemental materials.

In a preferred embodiment of the invention, the outer layer 42 comprises cellulose fiber reinforced agar gel.

According to the invention, the thickness of the outer layer 42 and/or material employed to form same can similarly be selected control to the on-set and rate of hydration of the foam 46. Residence time of the gastric device (40B and 40C) in the stomach is also similarly adjustable. In a preferred embodiment, residence time is in the range of approximately 1 hr.-2 weeks, or more.

In one embodiment of the invention, the foam 46 comprises a mechanically stable, high viscosity foam that is degradable by gastric fluid. Suitable high viscosity foams include, without limitation, polypeptide or protein, such as egg white or albumin, alone or in combination with substances, such as such as agar or related gums, that are not digestible inside the stomach.

In another embodiment of invention, the foam 46 comprises a foam gel. Suitable foam gels include, without limitation, any of the aforementioned gelling substance(s), which can be foamed in conventional ways, e.g., whipping, allowing gas to expand, or by producing gas in situ when the solution begins to gel, such as by adding acid to the bicarbonate containing solution. Foam stabilizing agents that are known in the art can also be used.

In a preferred embodiment, the foam 46 comprises foamed agar and egg white and the outer layer 42 comprises high gel strength agar impregnated with short cellulose fibers. The outer layer 42 is also sealed a layer of carrageenan on the inner surface.

Preferably, the gastric device 40A similarly has a delayed hydration period in the range of approximately 1 min.-30 min., more preferably, in the range of approximately 5 min.-10 min., and an expansion coefficient in the range of approximately 10-20. The device 40A also preferably reaches substantially full hydration and, hence, substantially full expansion in approximately 1-3 hrs.

Referring now to FIGS. 11A and 11B, there is shown a further embodiment of a gastric device of the invention. Referring first to FIG. 11A, there is shown the gastric device 50A prior to ingestion. As illustrated in FIG. 11A, the gastric device 50A similarly includes an outer region or layer 52, an internal cavity 54 and a gas producing member 56 disposed therein.

According to the invention, the gastric device 50A can similarly comprise a multitude of sizes and shapes. The gastric device 50A also preferably has dimensions similar to gastric devices 20A, 20D.

Referring now to FIG. 11B, there is shown an illustration of the device 50A after ingestion and hydration in the stomach (designated generally "50B"). As illustrated in FIG. 11B, when hydrated, the gas producing member 56 expands and releases a gas 51. The gas 51 and expanded member 56 fill and inflate the cavity 54, forming expanded device 50B.

According to the invention, the outer layer 52 can similarly be formed from food grade materials used to form outer layers 32, 42, which, as discussed above, are degradable (or erodible) by gastric fluid or intestinal contents. The outer layer 52 can also include one of the aforementioned reinforcing fibers and/or a viscosity building material and/or any of the aforementioned supplemental agents.

In a preferred embodiment of the invention, the outer layer 52 comprises high gel strength agar with uniformly dispersed insoluble fibers. Preferably, layer 52 and main body 56 comprise closed pore foam, which prevents rapid exchange of nutrients inside the stomach during the digestive process. Rapid exchange would defeat the large gastric volume displacement purpose of the device. A further advantage of closed pore foam is that abrasion of the outer surface layer will reveal another closed surface layer below.

According to the invention, the thickness of the outer layer 52 and/or material employed to form same can similarly be selected control to the on-set and rate of hydration of the gas producing member 56.

Residence time of the gastric device 50A in the stomach is also similarly adjustable. In a preferred embodiment, residence time is in the range of 2 hours-2 months, more preferably, 1-7 days.

In a preferred embodiment, the gas producing member 56 comprises a thin film or sheet of material that (i) forms a gas when hydrated and (ii) is degradable by gastric acid. Preferably, the member 56 is compressed to aid in delivery by reducing the size of the capsule to be ingested and to enhance the volume of the device 50b when the member 56 is hydrated. According to the invention, the member 56 can also be folded or rolled within cavity 54.

According to the invention, the member 56 can also be formed from various natural gel-forming substances or viscosity building materials, either with or without further crosslinking, alone or in combination, acacia (gum Arabic), agar, agarose, alginate gels or alginic acid, including non-cross linked and cross linked alginate gums, wherein the cross linked alginate gums can be cross linked with di- or trivalent ions, amylopectin, arbinoglactan, carob bean gum, carrageenan, chondroitin sulfate, eucheuma, fucoidan, furcellaran, gelatin, gellan, guar gum, gum ghatti, gum karaya, hypnea, karaya, laminaran, locust bean gum, natural gum, pectins, polypeptides, polyamino acids, tragacanth, and xanthan, like materials, and combinations and mixtures thereof.

In a preferred embodiment of the invention, the gas producing member 56 comprises preformed and dried agar gel. Such an embodiment is particularly desirable when secondary slow swelling times over many hours are required.

In one embodiment of the invention, the member 56 is preformed and over-coated with the layer of sodium bicarbonate-containing agar film. The subassembly is then over-coated with high gel-strength agar that contains a fine dispersion of cellulose fibers.

According to the invention, the member 56 can be formed (or processed) using various conventional processing methods. In one embodiment, the member 56 is made from a solution of hot agar that is allowed to gel in a desired shape.

According to the invention, liquid can be removed from the member 56 to form a dried film by any means known to those skilled in the art, including air-drying, freeze-drying, vacuum drying, or any other means of drying or dehydration known to those of skill in the art. Liquid can thus be removed from the member 56 by vacuum drying at room temperature. The member 56 can also be dehydrated by oven drying at a temperature of from about 35° C. to about 75° C. The member 56 can additionally be dehydrated by freeze drying.

Optionally, the dried member 56 can be compressed to a size and shape suitable for placement in the device cavity 56. Any means of compression known to those of skill in the art may be used, such as compression dies, by rolling, or by squeezing the dried film.

As will appreciated by one having skill in the art, the member material, size and shape can be tailored to further adjust or control the hydration rate and/or residence time.

Preferably, the gastric device 50A similarly has a delayed hydration period in the range of approximately 1 min.-30 min., more preferably, in the range of approximately 5 min.-10 min. and an expansion coefficient of at least 10, more preferably, in the range of 10-30. The device 50A also preferably reaches substantially full hydration and, hence, substantially full expansion in the range of approximately 1-3 hours.

Methods of using the gastric devices of the invention will now be described in detail. The methods set forth herein are merely examples of envisioned uses of the gastric devices to control and/or limit food intake and thus should not be considered as limiting the scope of the invention.

EXAMPLE 1

A 55 year old male is moderately obese, with a body mass index (BMI) of 30. He was of average weight until college, where he gained a significant amount of weight. He has tried several different diet and exercise routines over several years, but has never succeeded in losing a significant amount of weight, and tends to quickly gain back any that he does lose.

This patient will consult with a physician so that an accurate history can be taken. In this example, a major problem is portion control, as well as eating between meals. The physician and patient, and preferably a dietitian, will work out a regimen of diet and exercise. In coordination with this regimen, the patient will ingest a gastric device embodying features of the invention once a week. This gastric device is designed to form an expanded device approximately 100 cc in volume after ingestion with a residence time of approximately one week.

The patient will monitor his weight on a weekly basis, and continue taking the gastric devices on about a once-a-week basis. It is expected that by following this regimen with the aid of the gastric devices of the invention the patient will gradually lose weight over a 6 to 12 month period to reach a BMI of 25 or less.

EXAMPLE 2

A 30 year old female is slightly overweight, but is very concerned about how this affects her appearance. She has been unable to lose weight despite multiple attempts at dieting. She feels that her major problems in losing weight are "hunger pangs" and "cravings" between meals.

This patient will consult with a physician, who will prescribe gastric devices embodying features of the invention. In this example, the gastric devices are configured to form expanded devices approximately 30-50 cc in volume after hydration that will stay in the stomach a few hours. She will take one gastric device between meals to try to ameliorate any hungry feeling and she can take an additional gastric device if greater appetite control is needed. She will monitor her weight on a weekly basis.

EXAMPLE 3

A 40 year old male suffers from morbid obesity. He has been overweight since childhood, and his weight is now in excess of 200 percent of his ideal weight. He suffers from diabetes and sleep apnea, which his physician believes are directly related to his weight problem.

This patient will consult with a physician and dietician to work out a diet and walking regimen for long-term weight loss. In coordination with this regimen, the patient will start a program of taking gastric devices that embody features of the invention. In this example, the gastric devices are designed to form expanded devices of approximately 200 cc in volume after ingestion that will stay in the stomach for approximately one month.

In this example, the patient is told to monitor his weight weekly. It is expected that the patient will ingest one such gastric device approximately once a month for at least a year, and remain on the exercise and diet regimen during treatment.

EXAMPLE 4

An 18 year old athletic male is diagnosed with a malignancy. He undergoes chemotherapy. One of the side effects of the therapy is a dramatic increase in appetite, and he is "always hungry". This leads to a rapid weight gain of over 20 pounds from his normal baseline. This in turn, combined with other effects of his chemotherapy, causes a loss of self-esteem that his physicians worry could lead to depression.

This patient will consult with a physician. The patient will also receive extensive counseling and is advised to exercise as much as practical. As part of his treatment, this patient will be prescribed gastric devices embodying features of the invention. These gastric devices are designed to form expanded devices of approximately 50 cc in volume after ingestion that will stay in the stomach for approximately one day.

The patient's weight will be monitored weekly at regular appointments. It is expected that the patient will ingest one such gastric device approximately once a day, and remain on the program for the duration of his chemotherapy course.

As will be appreciated by one having ordinary skill in the art, the present invention provides numerous advantages. Among the advantages are the following:

1) The provision of a method and system for treatment of eating disorders that is low-risk, unobtrusive and noninvasive;

2) The provision of a method and system for treatment of eating disorders that applies controlled (and gentle) internal pressure to the upper portion of the stomach; particularly, the gastroesophageal sphincter;

3) The provision of an ingestible gastric device that minimizes or eliminates the possibility of esophageal expansion during ingestion;

4) The provision of a readily ingestible (i.e., easy to swallow) gastric device, which, when inflated, reduces the amount of food ingested to reach a feeling of fullness;

5) The provision of an ingestible, inflatable gastric device that substantially reduces or eliminates passage through the pyloric sphincter when inflated;

6) The provision of an inflatable, directive gastric device that allows food to pass through the stomach when inflated;

7) The provision of an ingestible, inflatable gastric device having a controlled rate of inflation and, hence, expansion;

8) The provision of an ingestible, inflatable gastric device that is inflated only in the presence of gastric acid, or alternatively, that is inflated in the partial or complete absence of gastric;

9) The provision of an ingestible, inflatable gastric device that is degradable (or dissoluble) by either gastric fluid, or by intestinal contents, or by both; and 10) The provision of an ingestible gastric device having a controlled rate of degradation.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A food grade ingestible gastric device, comprising:
a gas producing core material and an outer region, said gas producing core material and said outer region comprising food grade materials, said gas producing core material and said outer region forming a substantially solid structure, said outer region defining a first volume, said first volume allowing normal ingestion of said gastric device into a subject's stomach,
said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough,
said gastric device being adapted to hydrate after contact with said aqueous material for a period of time in the range of approximately 1-30 min,
said gastric device being adapted to sufficiently degrade in said subject's stomach after a first period of time to allow passage of said gastric device into said subject's duodenum,
said gastric device being further adapted to completely degrade in said subject's stomach and lower gastrointestinal tract.

2. A food grade ingestible gastric device, comprising:
a gas producing core material and an outer region, said gas producing core material and said outer region comprising food grade materials, said gas producing core material and said outer region forming a substantially solid structure, said outer region defining a first volume, said first volume allowing normal ingestion of said gastric device into a subject's stomach,
said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough,
said gastric device being adapted to hydrate to approximately 50% hydration after contact with said aqueous material for a period of time in the range of approximately 5 min.-3 hrs.,
said gastric device being adapted to sufficiently degrade in said subject's stomach after a first period of time to allow passage of said gastric device into said subject's duodenum,
said gastric device being further adapted to completely degrade in said subject's stomach and lower gastrointestinal tract.

3. A food grade ingestible gastric device, comprising:
a gas producing core material and an outer region, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said first period of time being in the range of approximately 1 week-3 months, said gastric device being further adapted to completely degrade in said subject's stomach and lower gastrointestinal tract.

4. A food grade ingestible gastric device, comprising:

a gas producing core material and an outer region, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said second volume being in the range of approximately 3-30 times greater than said first volume, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

5. A food grade ingestible gastric device, comprising:

a gas producing core material and an outer region, said gas producing core material and said outer region comprising food grade materials, said outer region further including reinforcing fibers, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

6. A food grade ingestible gastric device, comprising:

a gas producing core material and an outer region, said gas producing core material and said outer region comprising food grade materials, said outer region further including reinforcing fibers, said reinforcing fibers comprising soluble fibers comprising a material selected from the group consisting of carboxymethyl cellulose, methocel, carrageenan, guar gum, algimate gels, pectins, xanthan, gum Arabic (acacia), gum tragacanth, karaya, agar, gellan, alpha-polyhydroxy acids, polyglycolide (PGA), poly(L-lactide), poly(D,L-lactide), poly(.epsilon.-caprolactone), poly(trimethylene carbonate), poly(ethylene oxide) (PEO), poly(.beta.hydroxybutyrate) (PHB), poly(.beta.-hydroxyvalerate) (PHVA), poly(p-dioxanone) (PDS), poly(ortho esters), tyrosine-derived polycarbonates, like materials and mixtures thereof, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

7. A food grade ingestible gastric device, comprising:

a gas producing core material and an outer region, said gas producing core material and said outer region comprising food grade materials, said outer region further including reinforcing fibers, said reinforcing fibers comprising insoluble fibers comprising a material selected from the group consisting of insoluble polysaccharides, cellulose, phenylpropane molecules polymers, lignin, bast fibers, Kozo, Gampi, grasses, kenaf, bagasse, jute, hemp, flax, like materials and mixtures thereof, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

8. A food grade ingestible gastric device, comprising:

a gas producing core material and an outer region, said gas producing core material and said outer region comprising food grade materials, said outer region further including reinforcing fibers, said reinforcing fibers having a length in the range of approximately 0.1 mm-12 cm, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

9. A food grade ingestible gastric device, comprising:

a gas producing core material and an outer region, said gas producing core material and said outer region comprising food grade materials, said outer region comprising agar reinforced with cellulose fibers and coated with carrageenan, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

10. A food grade ingestible gastric device, comprising:

a gas producing core material and an outer region, said gas producing material comprising a high viscosity foam, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

11. A food grade ingestible gastric device, comprising:

a gas producing core material and an outer region, said gas producing material comprising a high viscosity foam, said high viscosity foam being selected from the group consisting of polypeptides proteins, egg white, and albumin, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

12. A food grade ingestible gastric device, comprising:

a gas producing core material and an outer region, said gas producing material comprising a high viscosity foam selected from the group consisting of polypeptides proteins, egg white, and albumin, said high viscosity foam further including a gel-forming agent, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

13. A food grade ingestible gastric device, comprising:

a gas producing core material and an outer region, said gas producing material comprising a high viscosity foam, said high viscosity foam further including a base, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

14. A food grade ingestible gastric device, comprising:

a gas producing core material and an outer region, said gas producing material comprising a high viscosity foam, said high viscosity foam further including a base, said high viscosity foam comprising alternating layers of an acid and said base, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

15. A food grade ingestible gastric device, comprising:

a gas producing core material and an outer region, said gas producing core material comprising a gas producing member configured to release gas and expand upon hydration, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

16. A food grade ingestible gastric device, comprising:

a gas producing core material and an outer region, said gas producing core material comprising a gas producing member configured to release gas and expand upon hydration, said gas producing member comprising a sheet of dried agar gel that forms a gas when hydrated and is degradable by gastric acid, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

17. A food grade ingestible gastric device, comprising:

a gas producing core material and an outer region, said gas producing core material comprising a gas producing member configured to release gas and expand upon hydration, said gas producing member comprising a sheet of dried agar gel that forms a gas when hydrated and is degradable by gastric acid, said agar gel sheet being overcoated with a layer of sodium bicarbonate-containing agar film, said gas producing core material and said outer region comprising food grade materials, said gas producing core material and said outer region forming a substantially solid structure, said outer region defining a first volume, said first volume allowing normal ingestion of said gastric device into a subject's stomach, said gas producing core material being adapted to produce a gas upon hydration of said gastric device with an aqueous material and thereby contact of said core material with said aqueous material, whereby said gastric device expands to a second volume greater than said first volume, said second volume being sufficient to preclude passage of said gastric device into said subject's duodenum while still allowing food to pass therethrough, said gastric device being adapted to sufficiently degrade in said subject's stomach after a first period of time to allow passage of said gastric device into said subject's duodenum, said gastric device being further adapted to completely degrade in said subject's stomach and lower gastrointestinal tract.

* * * * *